United States Patent [19]
Sugahara et al.

[11] Patent Number: 4,612,283
[45] Date of Patent: Sep. 16, 1986

[54] METHOD FOR PURIFICATION OF HBS ANTIGEN

[75] Inventors: Keishin Sugahara; Chikateru Nozaki; Fukusaburo Hamada; Fumio Miake; Nobuya Ohtomo, all of Kumamoto, Japan

[73] Assignee: 501 Juridical Foundation, The Chemo-Sero-Therapeutic Research Institute, Kumamoto, Japan

[21] Appl. No.: 656,315

[22] Filed: Oct. 1, 1984

[30] Foreign Application Priority Data

Oct. 5, 1983 [JP] Japan .................. 58-186187

[51] Int. Cl.$^4$ .................. C12P 21/00; A61K 39/29
[52] U.S. Cl. .................. 435/68; 424/88; 424/89; 530/403; 530/404; 530/406
[58] Field of Search .................. 435/68; 424/88, 89; 260/112 R

[56] References Cited

U.S. PATENT DOCUMENTS 4,301,250 11/1981 McAleer et al. .................. 435/241
4,442,205 4/1984 Hamer et al. .................. 435/68
4,515,714 5/1985 Kauahara et al. .................. 424/89

OTHER PUBLICATIONS

Hitzeman, R. et al., Nucleic Acid Research, vol. 11, pp. 2745-2763, 1983.

Primary Examiner—Blondel Hazel

[57] ABSTRACT

A method for purification of HBs antigen, which comprises treating an HBs antigen-containing material with an acid, optionally subjecting to salting out with ammonium sulfate, and subjecting the material to a chromatography with hydroxyapatite, by which a highly purified HBs antigen suitable for the preparation of HBV vaccine or diagnostic agent can be obtained in an industrial scale. This method is particularly useful for the purification of HBs antigen-containing material produced by recombinants obtained by DNA recombination technique.

14 Claims, No Drawings

METHOD FOR PURIFICATION OF HBS ANTIGEN

The present invention relates to a method for purification of HBs antigen (i.e. hepatitis B virus surface antigen). More particularly, it relates to an industrial method for purification of HBs antigen produced from a recombinant obtained by a DNA recombination technique.

TECHNICAL BACKGROUND AND TECHNICAL FIELD

Hepatitis B is usually induced by a hepatitis B virus (hereinafter, referred to as "HBV") and involves a major problem from immunological and clinical view points, but a sufficiently effective therapy has not yet been found. This disease is spread worldwidely and occurs particularly in Asia and Africa regions.

Effective prophylaxis of the disease is to administer an HBV vaccine and such a vaccine is practically used. The known HBV vaccine is usually prepared by highly purifying an HBs antigen obtained from blood plasma of a person infected inherently with HBV, so-called carrier, and inactivating the purified HBs antigen.

However, such a conventional vaccine must be subjected to safety tests in a chimpanzee in order to confirm that any infectious factors such as HBV or any other blood-origin viruses are not remaining in the vaccine, because it is obtained from blood. Besides, it is very difficult to get the chimpanzee for experiment. Thus, the conventional vaccine has some problems for industrial production thereof.

In order to eliminate such problems, many investigators have studied to obtain only HBs antigen on a large scale as the vaccine stock by utilizing DNA recombination technique, i.e. by introducing a DNA of HBV encoding HBs antigen protein into *Escherichia coli* or yeasts. Recently, it has been reported that the expression of HBs antigen by a recombinant was successful and the method could be used for the production of the antigen for practical use. Now, the last problem is how to purify the HBs antigen obtained by a recombinant in so high degree suitable for the desired vaccine stock or for diagnosis.

PRIOR ART

The commonly used purification methods of HBs antigen are a density gradient centrifugation [cf. Vyas, G. N. et al., J. Immunology, 108, 114 (1972)], a combination of a polyethylene glycol fractionation, gel filtration and centrifugation (cf. Japanese Patent Second Publication No. 21246/1982), and a combination of ammonium sulfate dialysis and gel filtration (cf. Japanese Patent First Publication No. 38617/1983). For the purification of HBs antigen obtained from a recombinant, there is also proposed a combination of an aqueous polymer two layer fractionation, ion exchange and gel filtration [cf. Hitzeman, R. A. et al, Nucleic Acid Research, 11, 2745 (1983)]. However, these methods can still not remove the problems in the purification of HBs antigen obtained from a recombinant and are hardly used as an industrial purification method.

In case of purification of HBs antigen obtained from a recombinant, there are some problems that the components contaminated in the starting materials, such as recombinant-originated proteins, lipids and other components, are essentially different from the contaminants in case of HBs antigen obtained from human blood not only in the kinds but also in the quantity, and that the amount of the contaminants in case of the HBs antigen obtained from a recombinant is far larger than that in case of the HBs antigen obtained from human blood. Besides, the present inventors have found that it has another problem that the HBs antigen is rapidly inactivated by a substance having a protease activity which is derived from the cells contaminated in the antigen. Accordingly, unless the substance having a protease activity is completely removed from the HBs antigen at a stage as early as possible, the yield of the HBs antigen is significantly decreased during the purification step. Moreover, the recombinant-origin HBs antigen has somewhat different affinity (biological affinity) from that of the human blood-origin HBs antigen. This is an additional problem for carrying the purification.

From these view points, the conventional purification methods applicable to the HBs antigen obtained from human blood are not satisfactorily applied for the purification of the recombinant-origin HBs antigen and for overcoming the specific problems involved therein. Even by the method of Hitzeman et al who have tried to purify a recombinant-origin HBs antigen, only a sample for biological analysis is obtained, but it can not give such a highly pure product that it can be used as a vaccine or a diagnostic product. They have studied neither the yield nor the deactivation of HBs antigen by a substance having a protease activity. Thus, such a method can not be used for the purification of a recombinant-origin HBs antigen on an industrial scale.

OBJECT OF THE INVENTION

The present inventors have intensively studied purification of a recombinant-origin HBs antigen on an industrial scale and have found that when an HBs antigen-containing material which is obtained from a culture broth of a recombinant and contains various cell-origin contaminants is acidified with an acid, most of the contaminated lipids and proteins which cause problems in a chromatography of the material can be removed and that the HBs antigen can be highly purified by subjecting it subsequently to a chromatography with hydroxyapatite.

An object of the present invention is to provide a purification method of HBs antigen obtained from a recombinant by a DNA recombination technique on an industrial scale, in a high efficiency and in a very high purity, which can give an HBs antigen suitable for preparing a stable and effective HBV vaccine. Another object of the invention is to provide an improved method for purification of a recombinant-origin HBs antigen by hydroxyapatite chromatography. These and other objects and advantages of the present invention are apparent to persons skilled in the art from the following description.

DETAILED EXPLANATION OF THE INVENTION

The method for the purification of HBs antigen produced by a recombinant utilizing a DNA recombination technique of the present invention comprises adding an acid to a starting material containing HBs antigen and cell-origin components to move the pH value to an acidic range, removing the resulting precipitates of lipids and contaminant proteins which cause problems in a chromatography, and subjecting the resultant mixture to an affinity chromatography with a hydroxyapatite, as it stands or optionally after subjected to conventional purification such as salting out and concentration with ammonium sulfate.

The starting HBs antigen-containing material used in the present invention is obtained by culturing a recombinant, which is obtained by a conventional transformation of microorganisms such as *E. coli* or an yeast so as to be able to produce the desired HBs antigen by a DNA recombination technique, in a suitable medium under suitable culture conditions to produce and accumulate HBs antigen in the culture broth, and then extracting roughly the HBs antigen in a conventional manner.

The recombinant-origin HBs antigen-containing material is usually obtained by a conventional DNA recombination technique, that is, by introducing an HBs antigen coding gene isolated from HBV DNA into a microorganism (e.g. *E. coli*, or an yeast) or an animal culture cell, by which the microorganism or animal cell is transformed with the gene, and producing HBs antigen by culturing the transformant under the action of HBs antigen gene. Such techniques have already been known. For instance, as a method for producing HBs antigen from a recombinant yeast, there are known a method of Valenzuela [cf. Valenzuela, Nature, 298, 347 (1982), and Japanese Patent First Publication No. 77823/1983], a method of Miyanohara et al. [cf. Proc. Natl. Acad. Sci., USA, 80, 1 (1983), and Japanese Patent First Publication No. 14246/1982], and a method of Hitzeman et al. [Hitzeman et al, Nucleic Acids Research, 11 (9), 2745 (1983), and Japanese Patent First Publication No. 109427/1983], and as a method for producing HBs antigen from a recombinant animal cells, there are known a method of Nozaki et al. (cf. 30th Japan Virus Association Meeting, Summary, p-1069 (1982), and Japanase Patent Application No. 145092/1982] and methods disclosed in other various literatures, such as Japanese Patent First Publication Nos. 56685/1983, 995/1984, and 39784/1982.

Extraction of HBs antigen from the culture broth is carried out by a conventional method, for example, by separating the cells from the culture broth by centrifugation, fracturing the cells in an appropriate buffer by a conventional method such as ultrasonic fracture, glass beads fracture, Manton-Gaulin fracture, or enzymatic dissolution of the cell walls, followed by fracturing the resulting spheroplast with a detergent, subjecting the fractured cells to centrifugation at a slow speed to remove the cell wall pieces, and further optionally filtering the mixture with a membrane filter to give an HBs antigen-containing material.

The acids used for acidifying the starting HBs antigen-containing material include all usually used acids, such as inorganic acids (e.g. hydrochloric acid, sulfuric acid, phosphoric acid) and organic acids (e.g. acetic acid, oxalic acid). The acidification is usually carried out by regulating the pH range of the starting mixture to pH 6 or lower, i.e. pH 5.0 to 6.0, preferably pH 5.0 to 5.5. The acidification treatment is preferably carried out at a temperature of not higher than 20° C., more preferably not higher than 10° C., i.e. at a range of 4° C. to 20° C., more preferably 4° C. to 10° C. After the pH regulation, the resulting precipitates are removed by centrifugation, and the supernatant containing HBs antigen is obtained.

When required, the HBs antigen-containing material is subjected to salting out and further to concentration with ammonium sulfate. For example, the HBs antigen-containing supernatant obtained after pH regulation as mentioned above is mixed with an aqueous ammonia to regulate to pH 6.0 to 8.0, and ammonium sulfate is added (e.g. 45 to 60% saturation) thereto while keeping the above pH range, and thereby HBs antigen is precipitated, which is separated from the supernatant by centrifugation. The precipitate thus separated is dissolved in an approximately neutral buffer having an ionic strength of about 0.001 to 1.0 (e.g. 0.1M phosphate buffer), and the solution is dialyzed against the same buffer used as above to give a material to be subjected to a chromatography with a hydroxyapatite.

Where the HBs antigen-containing supernatant is not subjected to a dialysis with ammonium sulfate, the material is regulated to pH 7.0 with an aqueous ammonia, and then subjected to dialysis with the same buffer likewise or diluted with the same buffer as above to give the material to be subjected to a chromatography with a hydroxyapatite.

The hydroxyapatite used in the present invention is calcium phosphate hydroxide which is a gel for a chromatography and is commercially available in the name of Hydroxyapatite (manufactured by Seikagaku Kogyo K.K. or Calbiochem-Behring Co.) and Hydroxylapatite (manufactured by Bio-Rad Co.). Chromatography of the HBs antigen-containing material with a hydroxyapatite is carried out in the following manner.

HBs antigen is adsorbed onto a hydroxyapatite by a column method or a batch method. In a case of column method, a column packed with a hydroxyapatite is equilibrated with the same buffer as used in the preparation of the material for chromatography as above (i.e. a buffer such as 0.1M phosphate buffer having a pH range of 6.0 to 8.0) through the column, and a material to be purified is passed through the equilibrated column to make the HBs antigen adsorbed onto the hydroxyapatite, by which undesirable contaminants such as substances having protease activity are separated. Thereafter, the column is washed with the same buffer as used for equilibration to wash out the contaminants, followed by eluting the HBs antigen from the column.

In case of a batch method, a hydroxyapatite equilibrated with the same buffer as above is added to an HBs antigen-containing material to be purified (usually in a mixing ratio of hydroxyapatite:HBs antigen-containing material of 1:20 to 1:200 in volume), and the mixture is slowly stirred for 0.5 to 2 hours, by which HBs antigen is adsorbed onto the hydroxyapatite. Thereafter, the hydroxyapatite adsorbing HBs antigen is filtered and washed with the same buffer for the equilibration. The filtration and washing are repeated for several times. Even in this batch method, the elution of the adsorbed HBs antigen from the hydroxyapatite is preferably carried out by packing the HBs antigen-adsorbed hydroxyapatite into a column, followed by eluting like in the column method as mentioned above.

The elution of the HBs antigen from the column is carried out stepwise or with concentration gradient of the eluant, wherein an approximately neutral buffer (pH 6.0 to 8.0, preferably 7.0) having an ionic strength larger than that of the buffer used for equilibration is used as the eluent. By the elution, fractions containing HBs antigen are separated. According to this method, the desired HBs antigen is highly and effectively purified. For the elution with the concentration gradient of the eluent, there can be used, for example, a concentration gradient of 0.1M→0.5M of a phosphate buffer, or a concentration gradient of 0.1M→1.0M of a sodium chloride-added phosphate buffer. There may also be used any other concentration gradient of appropriate buffers suitable for separation of the HBs antigen and contaminants. In stepwise elution, a buffer having an ionic strength suitable for eluting either HBs antigen or contaminants is firstly passed through the column, followed by passing through a buffer having a larger ionic strength suitable for eluting the remainder, by which a fraction containing the desired HBs antigen is taken out.

The chromatography with a hydroxyapatite is carried out at a temperature of 4° C. to 30° C., usually at 4° C. to 10° C. through whole step, i.e. from the adsorption to elution regardless of the column method or the batch method.

The HBs antigen thus obtained is preferably subjected to ultracentrifugation, such as sucrose step-gradient ultracentrifugation or sucrose linear-gradient ultracentrifugation, and optionally isopycnic ultracentrifugation or linear-gradient ultracentrifugation using cesium chloride, by which the HBs antigen is almost completely purified.

According to the present invention using a combination of an acid treatment—hydroxyapatite chromatography, the recombinant-origin HBs antigen can be effectively and highly purified in a simple operation and on industrial scale.

That is, since almost of the contaminants such as other proteins and lipids can be removed in the form of precipitates by the aid of acid treatment, the desired HBs antigen is well adsorbed onto the hydroxyapatite in an amount of more than 1 mg per 1 ml of hydroxyapatite, and hence, the required amount of the gel for chromatography and the scale of the apparatus can be made smaller. In the step of chromatography with a hydroxyapatite, the specific activity of HBs antigen (i.e. the ratio of the amount of HBs antigen/the amount of whole proteins contained therein) is increased about 100 to 150 times. Thus, the purification of HBs antigen is significantly increased.

Moreover, by the acid treatment and the chromatography with a hydroxyapatite, the substances having protease activities contained in the starting material are completely removed, and hence, the yield of the desired HBs antigen is as high as 50 to 60% (at the finish of chromatography). It should be mentioned that removal of the substances having protease activities is very important for purification of HBs antigen, because the substances significantly inactivate the HBs antigen. For instance, when a crude extract of the starting material which contains the substances having protease activities is kept at 4° C. or even at −20° C., HBs antigen is almost inactivated within about one week. Besides, under some conditions in the purification step, the protease activities are more promoted, and hence, the HBs antigen is occasionally more quickly inactivated.

The present inventors have tried to use various other gels for chromatography, such as DEAE cellulose, DEAE sepharose, CM cellulose, CM sepharose, cellulose phosphate, and blue dextrane sepharose, instead of the hydroxyapatite under various conditions, but the recombinant-origin HBs antigen could not be effectively purified, and further because of inactivation of HBs antigen, the yield was extremely low. Thus, the other conventional gels as mentioned above can not be used for the purification of a recombinant-origin HBs antigen in an industrial scale.

The HBs antigen purified by the hydroxyapatite chromatography of the present invention, followed by sucrose gradient ultracentrifugation and cesium chloride gradient ultracentrifugation, shows a single band in SDS-polyacrylamide gel electrophoresis, which means that the HBs antigen is quite pure.

The present invention is illustrated by the following Examples, but should not be construed to be limited thereto.

EXAMPLE 1

A recombinant yeast *Saccharomyces cerevisiae* AH 22/PAS 101 [cf. Proc. Natl. Acad. Sci., USA, 80, 1 (1983)] is cultured as described in the literature. The culture broth is centrifuged to collect the cells. To the cells thus obtained (about 1 kg) is added 0.1M phosphate buffer (pH 7.2) (5 liters), and the mixture is treated with a Manton-Gaulin fracturing machine under a pressure of 600 to 700 kg/cm$^2$ for seven times of passage to fracture the cells. The fractured cells are centrifuged to remove coarse pieces of the fractured cells to give a crude extract of HBs antigen having a concentration of HBs antigen of 1.3 μg/ml (measured by RIA kit, AUSRIA II, manufactured by Abbott, U.S.A.) and a concentration of proteins of 7.82 mg/ml (measured by Lowry method).

The crude extract is regulated to pH 5.2 by adding dropwise a 60% aqueous acetic acid while checking the pH value with a pH meter. After the mixture is stirred at 4° C. for about 30 minutes, the resulting precipitates are removed by centrifugation.

To the supernatant thus obtained is added aqueous ammonia to regulate the mixture to about pH 6.5, and thereto is added slowly ammonium sulfate so that the final concentration becomes 2.5M, while keeping the pH value as above. After allowing to stand for about 30 minutes, the mixture is centrifuged to take out precipitates containing HBs antigen. The precipitates thus obtained are suspended in 0.1M phosphate buffer (pH 7.2) (about 300 ml), and the mixture is dialyzed against about 100 times larger volume of the same buffer as used above in dialysis tubes.

After the dialysis, the mixture is diluted about 3 fold with 0.1M phosphate buffer, and then passed through a colum packed with a hydroxyapatite (gel content: about 1 liter) which column is previously equilibrated with the same buffer as above, by which HBs antigen is adsorbed onto the gel. The column is washed well with the same buffer as used for the equilibration, and then eluted with a phosphate buffer (about 4 liters) having a concentration gradient of 0.1M→0.5M to collect a fraction containing HBs antigen.

A 50% sucrose 0.01M phosphate buffered saline solution, a 20% sucrose 0.01M phosphate buffered saline solution and the HBs antigen-containing fraction thus obtained are entered in three layers (each 6 ml, 17 ml and 15 ml) in a ultracentrifugation tube for Beckman SW-28, and the tube is ultracentrifuged at 27,000 r.p.m. at 4° C. for 16 hours, by which HBs antigen is concentrated at around the interface of the sucrose solution layers.

The HBs antigen-containing fraction thus purified is dialyzed against 0.1M phosphate buffered saline solution, and thereto is added cesium chloride in a concentration of 1.2 g/ml. The mixture is concentrated by subjecting to ultracentrifugation with Beckman SW-28 at 25,000 r.p.m. at 10° C. for 60 hours to give purified HBs antigen.

The recovery rate of HBs antigen (i.e. the ratio to the amount of HBs antigen contained in the crude extract) and the ratio of the specific activity of HBs antigen to that of the crude extract (this means the rate of purification) in each step are shown in the following Table 1.

As is clear from the data, the rate of purification of the fraction eluted in the hydroxyapatite chromatography is 637 times compared with the crude extract. Thus, the method of the present invention is excellent for purification of HBs antigen.

TABLE 1

| Steps | Recovery rate (%) | Rate of purification |
| --- | --- | --- |
| Crude extract | 100 | 1 |
| Supernatant obtained after acid treatement | 90 | 1.7 |
| Precipitates by ammonium sulfate | 87 | 6.5 |
| HTP eluted fraction* | 32 | 637.0 |
| Fraction of sucrose ultra-centrifugation | 21 | 4140.5 |
| Fraction of CsCl ultracentrifugation | 18 | 4554.6 |

*HTP eluted fraction: The fraction obtained by the chromatography with a hydroxyapatite.

As to each sample obtained in the above steps, the protease activity was measured by using Protease Substrate Gel Tablets (manufactured by Bio Rad Co.). As a result, the crude extract showed protease activity corresponding to trypsin content about 800 μg/ml, and the precipitates by ammonium sulfate showed the activity of about 50 μg/ml, but the fraction of hydroxyapatite chromatography showed no protease activity.

EXAMPLE 2

A recombinant yeast *Saccharomyces cerevisiae* AH 22/PAH 203 [cf. Proc. Natl. Acad. Sci., USA, 80, 1 (1983)] is cultured as described in the literature. The culture broth is centrifuged to collect the cells. To the cells thus obtained (100 g) is added 0.1M phosphate buffer (pH 7.2) (500 ml), and the cells are fractured by sonication at lower than 10° C. for about 90 minutes. The fractured cells are centrifuged to remove coarse pieces of fractured cells to give a crude extract of HBs antigen. The crude extract is regulated to about pH 5.2 by adding dropwise hydrochloric acid while checking the pH value with a pH meter. After the mixture is stirred at 4° C. for about 30 minutes, the resulting precipitates are removed by centrifugation.

To the supernatant thus obtained is added aqueous ammonia to regulate the mixture to about pH 7.0, and the mixture is diluted about 3 to 5 folds with 0.1M phosphate buffer (pH 7.2), and then passed through a column packed with a hydroxyapatite which column is previously equilibrated with the same buffer as above, by which HBs antigen is adsorbed onto the gel. The column is washed well with the same buffer as used for the equilibration, and then a 0.2M phosphate buffer (pH 7.2, about 300 ml) is passed through the column in order to elute the contaminants adsorbed, and thereafter, a 0.5M phosphate buffer (pH 7.2, about 300 ml) is passed through the column to collect a fraction containing HBs antigen.

The HBs antigen-containing fraction thus obtained is subjected to sucrose ultracentrifugation and CsCl ultracentrifugation in the same manner as described in Example 1 to give purified HBs antigen.

The recovery rate of HBs antigen and the rate of purification in each step are shown in the following Table 2.

TABLE 2

| Steps | Recovery rate (%) | Rate of purification |
| --- | --- | --- |
| Crude extract | 100 | 1 |
| Supernatant obtained after acid treatment | 97 | 1.1 |
| HTP eluted fraction | 47 | 165.0 |
| Fraction of sucrose ultra-centrifugation | 34 | 1980.0 |
| Fraction of CsCl ultracentrifugation | 27 | 4950.0 |

The fraction of sucrose ultracentrifugation in Example 1 and the fraction of CsCl ultracentrifugation in Example 2 were each subjected to SDS-polyacrylamide gel electrophoresis. As a result, both fractions showed a single band of the subunit protein (molecular weight: about 24,000) composing HBs antigen, which means that the fractions are highly pure.

What is claimed is:

1. A method for purification of HBs antigen, which comprises treating an HBs antigen-containing material with an acid to adjust the pH value to a range of 5 to 6, removing the resulting precipitates, and subjecting the HBs antigen-containing solution to a chromatography with hydroxyapatite.

2. The method according to claim 1, wherein the HBs antigen-containing solution after acid treatment is subjected to salting out with ammonium sulfate.

3. The method according to claim 1, wherein the starting HBs antigen-containing material is a material produced by a recombinant being capable of producing HBs antigen which is obtained by a conventional DNA recombination technique.

4. The method according to claim 3, wherein the recombinant is a member selected from a recombinant *Escherichia coli* and a recombinant yeast.

5. The method according to claim 1, wherein the staring HBs antigen-containing material is a crude extract of HBs antigen which is obtained by subjecting recombinant cells to ultrasonic fracture, glass beads fracture, Manton-Gaulin fracture or treatment with a detergent.

6. The method according to clam 1, wherein the acid is a member selected from the group consisting of hydrochloric acid, sulfuric acid, phosphoric acid, acetic acid and oxalic acid.

7. The method according to claim 1, wherein the acid treatment is carried out at a pH range of 5 to 6 and at a temperature of 4° C. to 20° C.

8. The method according to claim 1, wherein the chromatography with hydroxyapatite is carried out by a column method or a batch method.

9. The method according to claim 8, wherein the chromatography with hydroxyapatite is carried out by a column method which comprises equilibrating a column packed with hydroxyapatite with a buffer having a pH range of 6 to 8, passing through the equilibrated column the HBs antigen-containing solution, washing the column with the same buffer as used for equilibration, and eluting the adsorbed HBs antigen with a buffer having a pH range of 6 to 8.

10. The method according to claim 9, wherein the elution is carried out stepwise by first passing through a buffer having a pH range of 6 to 8 and a concentration of 0.1M to 0.2M to remove the contaminants and secondly passing through a buffer having a pH range of 6 to 8 and a concentration of 0.5M to 1.0M to elute out the HBs antigen.

11. The method according to claim 9, wherein the elution is carried out with a concentration gradient of an eluent using a buffer selected from a phosphate buffer having a concentration gradient of 0.1M→0.5M and a sodium chloride-added phosphate buffer having a concentration gradient of 0.1M→1.0M.

12. The method according to claim 8, wherein the chromatography with hydroxyapatite is carried out by a batch method which comprises equilibrating hydroxyapatite with a buffer having a pH range of 6 to 8 and a concentration of 0.1M to 0.2M, mixing the equilibrated hydroxyapatite with the HBs antigen-containing material, washing the hydroxyapatite with the same buffer as used for equilibration, and then eluting the HBs antigen adsorbed onto the hydroxyapatite.

13. The method according to claim 12, wherein the elution of HBs antigen is carried out with a buffer having a pH range of 6 to 8.

14. The method according to claim 12, wherein the elution of HBs antigen is carried out with a concentration gradient of an eluent using a buffer selected from a phosphate buffer having a concentration gradient of 0.1M→0.5M and a sodium chloride-added phosphate buffer having a concentration gradient of 0.1M→1.0M.

* * * * *